US005618983A

United States Patent [19]
Burke

[11] Patent Number: 5,618,983
[45] Date of Patent: Apr. 8, 1997

[54] HYDROFORMYLATION PROCESS

[75] Inventor: Patrick M. Burke, Wilmington, Del.

[73] Assignees: E. I. Du Pont de Nemours and Company, Wilmington, Del.; DSM N. V., Galeen, Netherlands

[21] Appl. No.: 519,833

[22] Filed: Aug. 25, 1995

[51] Int. Cl.$^6$ ................................................. C07C 45/50
[52] U.S. Cl. ............................ 568/454; 568/451; 568/455
[58] Field of Search ................................ 568/451, 454, 568/455

[56] References Cited

U.S. PATENT DOCUMENTS 4,283,563  8/1981  Kawabata et al. ..................... 568/454
4,301,090  11/1981  Pesa et al. ........................... 260/465.4
4,528,278  7/1985  Hsu ....................................... 502/153

*Primary Examiner*—Porforio Nazario-Gonzalez
*Assistant Examiner*—S. Padmanabhan

[57] ABSTRACT

A hydroformylation process for the production of linear aldehydes from linear olefins, by the reaction of the olefin with hydrogen and carbon monoxide in a solvent containing a catalyst having a platinum component or palladium component, a bidentate diaryl phosphine component where the bridging group is ferrocenyl or 3 to 6 carbon atoms, and a metal promoter component.

11 Claims, No Drawings

HYDROFORMYLATION PROCESS

FIELD OF THE INVENTION

This invention relates to the hydroformylation of olefins to form the corresponding aldehydes.

BACKGROUND OF THE INVENTION

Botteghi et al. in *Journal of Organometallic Chemistry* 417 (1991) C41–C45 in an article titled "Hydroformylation of olefins catalyzed by alkene complexes of platinum(0)" disclose hydroformylation using a bidentate phospino compound, a platinum catalyst, and an acid promoter in an organic solvent. This article notes: ". . . , internal double bonds are rather unreactive as shown by the hydroformylation of cyclohexene . . . ".

An object of the present invention is to provide a process for the hydroformylation of internally unsaturated olefins or terminally unsaturated olefins to form particular linear aldehyde products.

SUMMARY OF THE INVENTION

The present invention is a process for the preparation of linear aldehydes which comprises contacting a linear olefin, hydrogen, water, and carbon monoxide in an organic solvent containing a dissolved catalyst comprising: (a) a platinum compound free of anionic halide or palladium compound free of anionic halide, (b) a bidentate diaryl phosphine ligand where each of the aryl groups contain up to 15 carbon atoms and where the bridging group contains 3 to 6 carbon atoms or is a ferrocenyl group, and (c) a promoter selected from the group consisting of (i) a metal perfluoroalkane sulfonate where the alkane has 1 to 10 carbon atom, (ii) a metal perfluoro-betadiketonate of up to 11 carbon atoms, and (iii) a metal trifluoroacetate; where the metal in (i), (ii), and (iii) is selected from the group consisting of aluminum, scandium, nickel, zinc, yttrium, zirconium, tin, lanthanum, and lanthanide elements from praseodymium to lutetium; where the ratio of (c) to (a) is in the range of 0.5/1 to 20/1, and the ratio of (b) to (a) is in the range of 0.8/1 to 1.5/1.

Preferably the olefin contains 2 to 10 carbon atoms. One preferred olefin is 3-pentenenitrile and the linear aldehyde product is 5-formylvaleronitrile. Another preferred olefin is a methyl pentenoate and the linear aldehyde product is methyl-5-formylvalerate.

The process will usually be carried out at a temperature in the range of 80° to 120° C. and the carbon monoxide pressure in the range of 500 to 3000 pounds per square inch.

The present invention is also a composition comprising organic solvent containing a dissolved catalyst comprising: (a) a platinum compound free of anionic halide or palladium compound free of anionic halide, (b) a bidentate diaryl phosphine ligand where each of the aryl groups contains up to 15 carbon atoms, where the bridging group contains 3 to 6 carbon atoms or is a ferrocenyl group, and (c) a promoter selected from the group consisting of (i) a metal perfluoroalkane sulfonate where the alkane has 1 to 10 carbon atoms, (ii) a metal perfluoro-betadiketonate of up to 11 carbon atoms, and (iii) a metal trifluoroacetate; where the metal in (i), (ii), and (iii) is selected from the group consisting of aluminum, scandium, nickel, zinc, yttrium, zirconium, tin, lanthanum, and lanthanide elements from praseodymium to lutetium; where the ratio of (c) to (a) is in the range of 0.5/1 to 20/1, and the ratio of (b) to (a) is in the range of 0.8/1 to 1.5/1.

In both the process and the composition the ratio of water to metal promoter is 200:1 or less.

Preferably the linear olefin contains 4 to 10 carbon atoms.

Suitable solvents include acetonitrile, adiponitrile, methylglutaronitrile, dimethyladipate, valerolactone, methylisobutylketone, dimethylacetamide, dimethylformamide, methylene chloride, mixtures of one of the above nitriles and toluene, and homogeneous mixtures of the above nitriles and water. The solvent may also be an alkanol containing 1 to 6 carbon atoms, for example methanol or ethanol. In these cases the product will be the acetal of the aldehydes formed in the hydroformylation reaction. The catalysts of this invention are therefore dual functional in that they catalyze both the hydroformylation and acetalization reactions simultaneously. When the process of the present invention is operated in a continuous manner, the product will be removed from the solvent and the solvent recycled, and gradually the composition of the solvent will change as more and more by-products of the reaction remain in the recycled solvent.

Preferred bidentate diaryl phosphine ferrocene ligands having the formula Ar2P-Q-PAr2 include: 1,1'-Bis(diphenylphosphino)ferrocene, sometimes referred to hereinafter as DPPF; 1,1'-Bis(di-m-fluorophenylphosphino)ferrocene; 1,1'-Bis(di-p-methylphenylphosphino)ferrocene; and 1,1'-Bis(diphenylphosphino )3,3'-(trimethylsilyl)ferrocene.

Preferred bidentate diaryl phosphine ligands having bridging groups of 3 to 6 carbon atoms include: (+)2,3-O-Isopropylidine-2,3-dihydroxy-1,4-bis(diphenylphosphino)butane; sometimes referred to hereinafter as DIOP; (–)-(2S,4S)-2,4-Bis(diphenylphosphino)pentane; sometimes referred to hereinafter as S,S-BDPP; 1,3-Bis(diphenylphosphino)propane; sometimes referred to hereinafter as DPPP; (S)-(–)-2,2'-Bis(diphenylphosphino)-1,1'-binapthyl sometimes referred to hereinafter as BINAP; and 1,4-Bis(diphenylphosphino)butane sometimes referred to hereinafter as DPPB.

DETAILED DESCRIPTION OF THE INVENTION

Suitable olefins for hydroformylation into linear aldehydes include: (1) pentenoic acid esters such as 2-and 3-pentenoic acid esters where the non-pentenoic acid portion is from a hydrocarbon alcohol. The hydrocarbon alcohol may be saturated or unsaturated, aliphatic or aromatic but usually will have from 1 to 8 carbon atoms. (2)2-and 3-pentenenitrile (3) hexene-1 and hexene-2, etc. The olefin may be an internal olefin or a terminal olefin. The olefin may be substituted with other groups such as carboxyl, ester, nitrile, aldehyde, or ketone groups.

The organic solvent for use in the process should dissolve the platinum catalyst compound or the palladium catalyst compound, the compound to be hydroformylated, the bidentate diarylphosphine ligand, the promoter, and the product. Stated another way, the solvent should provide a homogeneous reaction mixture. Suitable solvents include acetonitrile, adiponitrile, methylglutaronitrile, dimethyladipate, caprolactone, dichloromethane, 2-butanone, propylenecarbonate, valerolactone, methylisobutylketone, methylene chloride, mixtures of one of the above nitriles and toluene, and homogeneous mixtures of the above nitriles and water. When the process of the present invention is operated in a continuous manner, the product will be removed from the solvent and the solvent recycled, and gradually the composition of the solvent will change as more and more by-products of the reaction remain in the recycled solvent.

The platinum component or the palladium component of the catalyst must be free of anionic halide but may contain covalent halide, e.g., fluorinated betadiketonate. Platinum(II) or palladium(II) beta-diketonate, platinum(II) or palladium(II) carboxylates, and platinum or palladium complexes such as Pt(cyclooctadiene)2 or Pd(cyclooctadiene)2 may be the catalyst component.

The promoter is selected from the group consisting of: (i) a metal perfluoroalkane sulfonate where the alkane has 1 to 10 carbon atoms, (ii) a metal perfluoro-betadiketonate of up to 11 carbon atoms, and (iii) a metal trifluoroacetate; where the metal in (i), (ii), and (iii) is selected from the group consisting of aluminum, scandium, nickel, zinc, yttrium, zirconium, tin, lanthanum, and lanthanide elements from praseodymium to lutetium. Specific promoters from the above groups that are effective are: lanthanum, or dysprosium, or neodynium, or ytterbium trifluoromethanesulfonate; neodymium, or zirconium, or ytterbium, or scandium, or praseodymium, or lanthanum, hexafluoroacetylacetonates.

The bidentate diaryl phosphine ligand having the formula Ar2P-Q-PAr2 where Q is a ferrocenyl group and each of the Ar groups contain 6 to 15 carbon atoms include such compounds s 1,1'-Bis(diphenylphosphino)ferrocene; 1,1'-Bis(di-m-fluorophenylphosphino)ferrocene; 1,1'-Bis(di-p-methylphenyl-phosphino)ferrocene; 1,1'-Bis(diphenylphosphino)3,3'-trimethylsilyl)ferrocene; 1,1'-Bis(di-p-trifluoromethylphenylphosphino)ferrocene and 1,1'-Bis(di-3,5-(bis)trifluoromethyl)phenylphosphino)ferrocene, and where Q is a bridging group containing 3 to 6 carbon atoms (+)2,3-O-Isopropylidine-2,3-dihydroxy-1,4-bis(diphenylphosphino)butane; (−)-(2S,4S)-2,4-Bis(diphenylphosphino)pentane; 1,3-Bis(diphenylphosphino)propane; (S)-(−)-2,2'-Bis(diphenylphosphino)-1,1'-binapthyl.

EXAMPLE 1

M3P Hydroformylation with Pt(AcAc)2/DPPF/La(OSO3CF3)3

A 25 ml glass lined shaker tube was charged with 5 ml of a solution containing 11.4 g (100 mmole) methyl-3-pentenoate (M3P), 0.393 g (1.0 mmole) platinum(II) acetylacetonate (Pt(AcAc)2), 0.70 g (1.26 mmole) 1,1'-Bis(diphenylphosphino)ferrocene (DPPF), 2.93 g (5 mmoles) lanthanum trifluoromethane sulfonate La(OSO3CF3)3, 0.2 g (11 mmoles) water and 1.00 g o-dichlorobenzene (ODCB, internal GC standard) in 100 ml of a 4:1 mixture of toluene and acetonitrile. The solution contained 0.05 mg-atom Pt and a Pt(AcAc)2/DPPF/La(OSO3CF3)3/H20 mole ratio of 1:1.26:5:11.

The shaker tube was freed from air by purging first with 100 psi nitrogen (twice) and then with 1:1 CO/H2 (twice). The tube was then pressurized to 700 psi CO/H2 and heated 100° C. over 30 minutes. The pressure was then adjusted with 1:1 CO/H2 to 1000 psi at 100° C. The temperature was maintained at 100° C. with shaker agitation for 2 hours. The heat was shut off and the shaker tube was allowed to cool to 25–35° C. The excess CO/H2 was vented and the product was analyzed for methyl esters and formylvalerates on a capillary GC column. The analysis showed (in g/100 ml):

| Conversion Selectivities | 21.4% |
|---|---|
| Methyl-5-formylvalerate (M5FV) | 82.8 |
| Methyl-4-formylvalerate (M4FV) | 6.1 |
| Methyl-3-formylvalerate (M3FV) | 0.8 |
| Methyl-4-pentenoate (M4P) | 3.0 |
| Cis-methyl-2-pentenoate (CM2P) | 0.8 |
| Trans-methyl-2-pentenoate (TM2P) | 3.7 |
| Methylvalerate (MV) | 2.9 |
| Accounting (sum of all analyzed products and starting material): | 99% |

The yield to the desired product, methyl-5-formylvalerate (M5FV), is 82.8% at 21% conversion and the linearity (100* M5FV/(M5FV+M4FV+M3FV)) is 92.3%.

The example illustrates the very high selectivity to linear aldehyde from an internal olefin that may be obtained with the catalyst of this invention.

In the following examples the products were analyzed in the same way but the results are expressed in summary form as combined conversion of M3P and M4P ("Conv"), Selectivity to methyl-5-formylvalerate ("Sel"), linearity and product accounting ("Acctg").

EXAMPLES 2–9

1. Promotion with Metal Trifluoromethanesulfonates
a. DPPF Ligand and Various Metal Trifluoromethanesulfonates
M3P Hydroformylation with Pt(AcAc)2/DPPF/M(OSO3CF3)3 The experiment in Example 1 was repeated except that the lanthanum trifluoromethanesulfonate was replaced with an equivalent amount of other metal trifluoromethanesulfonates and the mole ratios of trifluoromethanesulfonate to platinum and of water to metal trifluoromethanesulfonate were varied. The results are shown in Table 1.

TABLE 1

| Ex. | Metal | M/Pt | H$_2$O/M | Conv | Sel | Lin | Acctg |
|---|---|---|---|---|---|---|---|
| 2 | La | 5 | 0 | 35 | 84 | 94 | 99 |
| 3 | La | 5 | 3 | 54 | 81 | 93 | 96 |
| 4 | La | 5 | 1 | 51 | 81 | 94 | 98 |
| 5 | Dy | 5 | 0 | 64 | 56 | 80 | 89 |
| 6 | Dy | 5 | 1 | 79 | 53 | 80 | 87 |
| 7 | Dy | 1 | 0 | 14.3 | 78 | 91 | 96 |
| 8 | Nd | 5 | 0 | 82 | 52 | 80 | 95 |
| 9 | Yb | 1 | 2 | 24.5 | 79 | 91.0 | 95.3 |

These examples show that the hydroformylation reaction may be promoted with a variety of metal trifluoromethanesulfonates.

EXAMPLES 10–17 b. Lanthanum Trifluoromethanesulfonate and Various Bidentate Phosphine Ligands
M3P Hydroformylation with Pt(AcAc)2/LIGAND/La(OSO3CF3)3

The experiment in Example 1 was repeated except that the DPPF ligand was replaced with an equivalent amount of other bidentate phosphine ligand and the water to metal ratio was varied. The results as shown in Table 2.

TABLE 2

| Ex. | Ligand | M/Pt | H$_2$O/M | Conv | Sel | Lin | Acctg |
|---|---|---|---|---|---|---|---|
| 10 | DIOP | 5 | 1 | 29 | 72 | 83 | 98 |
| 11 | DIOP | 5 | 0 | 26 | 73 | 85 | 97 |

TABLE 2-continued

| Ex. | Ligand | M/Pt | H₂O/M | Conv | Sel | Lin | Acctg |
|---|---|---|---|---|---|---|---|
| 12 | (S,S)-BDPP | 5 | 0 | 58 | 61 | 85 | 85 |
| 13 | DPPP | 5 | 0 | 13 | 44 | 62 | 101 |
| 14 | BINAP | 5 | 0 | 1.3 | 37 | 89 | 102 |
| 15 | DPPB | 5 | 0 | 25 | 61 | 70 | 98 |
| 16 | DPPB | 5 | 1 | 24 | 69 | 80 | 97 |
| 17 | DPPB | 5 | 3 | 15 | 74 | 85 | 100 |

DIOP = (+)2,3-O-Isopropylidine-2,3-dihydroxy-1,4-bis(diphenylphosphino)butane
(S,S)-BDPP = (−)-(2S,4S)-2,4-Bis(diphenylphosphino)pentane
DPPP = 1,3-Bis(diphenylphosphino)propane
BINAP = (S)-(−)-2,2'-Bis(diphenylphosphino)-1,1'-binaphthyl
DPPB = 1,3-Bis(diphenylphosphino)butane These examples show that good selectivity can be obtained with a variety of bidentate phosphine ligands containing a 3 or 4 carbon chain between the phosphorus atoms.

EXAMPLES 18–28

2. Promotion with Metal Hexafluoroacetylacetonates a. DPPF Ligand and Various Metal Hexafluoroacetylacetonates M3P Hydroformylation with Pt(AcAc)2/DPPF/M(HFAA)n The experiment in Example 1 was repeated except that the lanthanum triflate was replaced with an equivalent amount of various metal hexafluoroacetylacetonates and the mole ratios of metal HFAA to platinum and of water to metal HFAA were varied. The results are shown in Table 3.

TABLE 3

| Ex. | HFAA | M/Pt | H₂O/M | Conv | Sel | Lin | Acctg |
|---|---|---|---|---|---|---|---|
| 18 | Nd(III) | 2 | 2 | 13 | 80 | 92 | 99 |
| 19 | Nd(III) | 5 | 2 | 33 | 82 | 92 | 94 |
| 20 | Nd(III) | 10 | 2 | 42 | 82 | 91 | 91 |
| 21 | Zr(IV) | 5 | 2 | 29 | 82 | 93 | 98 |
| 22 | Y(III) | 5 | 2 | 16 | 80 | 91 | 95 |
| 23 | Y(III) | 5 | 0 | 17 | 69 | 87 | 100 |
| 24 | Sc(III) | 5 | 2 | 61 | 71 | 93 | 70 |
| 25 | Sc(III) | 5 | 0 | 51 | 74 | 93 | 75 |
| 26 | Pr(III) | 5 | 3 | 30 | 80 | 93 | 90 |
| 27 | Zn(II) | 5 | 2 | 16 | 76 | 92 | 101 |
| 28 | Al(III) | 5 | 2 | 24 | 61 | 91 | 103 |

DPPF = 1,1'-Bis(diphenylphosphino)ferrocene

These examples show that a wide variety of metal hexafluoroacetylacetonates are active promoters for the hydroformylation.

EXAMPLE 29

Activity Demonstration: Hydroformylation of M3P with Pt(AcAc)2/DPPF/La(OTf)3 at 100° C. and 1000 psi A 160 ml mechanically stirred zirconium autoclave was flushed with nitrogen and then with 600 psi of 1:1 CO/H2. It was then charged with a solution of 0.35 g (0.62 mmole) DPPF ligand, 1.46 g (2.5 mmole) lanthanum triflate promoter, 0.13 g (7.5 mmole) water and 32.4 g 4:1 toluene/acetonitrile solvent. The autoclave was pressured with 1:1 CO/H2 to 700 psi and heated to 100° C. The reaction was initiated by adding a solution of 5.0 grams (44 mmole) of M3P and 0.5 g ODCB internal GC standarded in 10 g 4:1 toluene/acetonitrile solvent. The pressure was immediately adjusted with CO/H2 to 1000 psi at 100° C. CO/H2 was continuously fed to the autoclave from a reservoir so as to maintain the total pressure constant at 1000 psi. Samples were removed at intervals for GC analysis. The reaction was allowed to run for a total of 3 hours after which it was cooled to 20° C. The excess CO/H2 was vented through a control valve and the product was discharged.

The samples from the reactor were analyzed on a 30m Carbowax capillary GC column. The results are shown below.

| Time (Min) | Conversion (%) | Selectivity (% M5FV) | Linearity (%) |
|---|---|---|---|
| 15 | 8.2 | 91.7 | 93.6 |
| 60 | 15.6 | 90.2 | 93.7 |
| 120 | 30.2 | 89.1 | 92.5 |
| 180 | 44.4 | 89.1 | 92.5 |
| 240 | 55.2 | 88.9 | 92.6 |

The first order rate constant is 0.2/Hr and the turnover frequency from this rate is 72 moles/mole Rh/Hr.

This example illustrates that the reaction is first order in pentenoate to at least 50% conversion.

EXAMPLES 30–36

Hydroformylation of Hexenes with Pt(AcAc)2/DPPF/+Promoter

The experiment in Example 1 was repeated except that the M3P was replaced by Hexene-1, trans-Hexene-2 or trans-Hexene-3, the promoter was varied and the mole ratio of water to promoter was varied. The results are shown in Table 4.

TABLE 4

| Ex. | BH Ex. No. | Olefin | Promoter (P) | H₂O/P | Conv | Sel to n-Heptanal |
|---|---|---|---|---|---|---|
| 30 | 112-1b | 1-Hexene | La(OSO₃CF₃)₃ | 10 | 56 | 93 |
| 31 | 112-2b | 1-Hexene | Nd(HFAA)3 | 10 | 27 | 85 |
| 32 | 112-4b | 1-Hexene | Dy(OSO₃CF₃)₃ | 0 | 10 | 71 |
| 33 | 112-1c | t-2-Hexene | La(OSO₃CF₃)₃ | 10 | 6.6 | 86 |
| 34 | 112-2d | t-3-Hexene | Nd(HFAA)3 | 10 | 18 | 86 |
| 35 | 112-2e | t-2-Hexene | Nd(HFAA)3 | 10 | 23 | 89 |
| 36 | 112-4d | t-3-Hexene | Dy(OSO₃CF₃)₃ | 0 | 23 | 84 |

These examples illustrate that high selectivity can be obtained with both terminal and internal olefins with the catalyst of this invention.

EXAMPLES 37–42

Hydroformylation of Pentenoic Acids with Pt(AcAc)2+Ligand +Promoter

The experiment in Example 1 was repeated except that the M3P was replaced by 3-pentenoic acid (3PA) or 4-pentenoic acid (4PA) and both the promoter and phosphorus ligand were varied and the reaction was allowed to run for 4 hours. The results are shown in Table 5.

TABLE 5

| Ex. | Olefin | Ligand | Promoter (P) | H$_2$O/P | Conv | Sel to 5FVA | Lin |
|---|---|---|---|---|---|---|---|
| 37 | 3PA | DPPF | La(OSO$_3$CF$_3$)$_3$ | 10 | 72 | 51 | 72 |
| 38 | 3PA | DPPF | Nd(HFAA)3 | 10 | 87 | 83 | 89 |
| 39 | 3PA | DIOP | Nd(HFAA)3 | 10 | 87 | 81 | 96 |
| 40 | 3PA | DIOP | La(OSO$_3$CF$_3$)$_3$ | 10 | 42 | 44 | 75 |
| 41 | 4PA | DPPF | La(OSO$_3$CF$_3$)$_3$ | 10 | 70 | 54 | 74 |
| 42 | 4PA | DPPB | La(OSO$_3$CF$_3$)$_3$ | 10 | 68 | 21 | 76 |

These experiments illustrate the application of the catalyst to olefins that contain a carboxylic acid function.

EXAMPLE 43

The experiment in Example 1 was repeated except that the M3P was replaced by 3-pentenenitrile (6M Concentration) and the solvent was toluene. After 6 hours the conversion of 3PN was 6.8%, the selectivity to 5-formylvaleronitrile was 45% and the linearity was 88.4%.

This example illustrates the applicability of the catalyst to internal olefins containing a nitrile function.

EXAMPLES 44–50

Hydroformylation of M3P was Pt(AcAc)2+DPPF+Metal Trifluoroacetate

The experiment in Example 1 was repeated except that the promoter was a trifluoroacetate and the water/promoter and promoter/Pt ratios were varied. The results are shown in Table 6.

TABLE 6

| Ex. | BH Ex. No. | Promoter (P) | P/Pt | H$_2$O/P | Conv | Sel to M5FV | Lin |
|---|---|---|---|---|---|---|---|
| 44 | 123-1a | Y(OCOCF3)3 | 5 | 0 | 8.8 | 80 | 92 |
| 45 | 124-4b | Y(OCOCF3)3 | 10 | 0 | 38 | 67 | 89 |
| 46 | 125-2a | Y(OCOCF3)3 | 10 | 2 | 28 | 52 | 86 |
| 47 | 134-1b | La(OCOCF3)3 | 5 | 0 | 35 | 83 | 92 |
| 48 | 134-1d | Dy(OCOCF3)3 | 5 | 0 | 34 | 67 | 89 |
| 49 | 134-2b | Er(OCOCF3)3 | 5 | 0 | 37 | 78 | 90 |
| 50 | 134-2d | Yb(OCOCF3)3 | 5 | 0 | 34 | 81 | 91 |

These examples illustrate the activity of trifluoroacetates of a variety of metals for the hydroformylation reaction.

EXAMPLE 51

Hydroformylation of M3P with Pd(AcAc)2+DPPP+La(OSO$_3$CF$_3$)$_3$ in Dimethylacetamide (DMAc) Solvent A 25 ml glass lined shaker tube was charged with 5 ml of a solution containing 11.4 g (100 mmole) methyl-3-pentenoate (M3P), 0.304 g (1.0 mmole) palladium(II) acetylacetonate (Pd(AcAc)2), 0.52 g (1.26 mmole), 1,3'-bis(diphenylphosphino)propane, 2.93 g (5 mmoles) lanthanum trifluoromethane sulfonate (LA(OSO$_3$CF$_3$)3) and 1.00 g o-dichlorobenzene (ODCB, internal GC standard) in 100 ml of dimethylacetamide. The solution contained 0.05 mg-atom Pd and a Pd(AcAc)2/DPPF/La(OSO$_3$CF$_3$)$_3$ mole ratio of 1:1.26:5.

The shaker tube was freed from air by pressurizing and depressurizing first with 100 psi nitrogen (twice) and then with 1:1 CO/H2 (twice). The tube was then pressurized to 700 psi CO/H2 and heated 100° C. over 30 minutes. The pressure was then adjusted with 1:1 CO/H2 to 1000 psi at 100° C. The temperature was maintained at 100° C. with shaker agitation for 2 hours. The heat was shut off and the shaker tube was allowed to cool to 25°14 35° C. The excess CO/H2 was vented and the product was analyzed for methyl esters and formylvalerates on a capillary GC column. The results are shown in Table 7.

EXAMPLE 52

Hydroformylation of M3P with Pd(AcAc)2+DPPP+La(OSO$_3$CF$_3$)$_3$ in Dimethylacetamide (DMAc) Solvent The experiment in Example 51 was repeated except that the M3P was replaced with M4P. The result are summarized in Table 7.

EXAMPLES 53–56

Hydroformylation of M3P with Pd(AcAc)2+Ligand+Promoter in Dimethylacetamide (DMAc) Solvent The experiment in Example 51 was repeated except that ligand and promoter were varied. The results are summarized in Table 7.

TABLE 7

| Ex. | Olefin | Ligand | Promoter | Conv | Sel to 5FVA | Lin |
|---|---|---|---|---|---|---|
| 51 | M3P | DPPP | La(OSO$_3$CF3)$_3$ | 15 | 51 | 60 |
| 52 | M4P | DPPP | La(OSO$_3$CF3)$_3$ | 28 | 64 | 67 |
| 53 | M3P | S,S-BDPP | La(OSO$_3$CF3)$_3$ | 20 | 40 | 63 |
| 54 | M3P | DPPP | Dy(OSO$_3$CF3)$_3$ | 10 | 53 | 60 |
| 55 | M3P | DPPP | Al(HFAA)3 | 7.3 | 42 | 52 |
| 56 | M3P | DPPP | Sc(OSO$_3$CF3)$_3$ | 8.9 | 51 | 61 |

The above examples illustrate the application of the metal trifluoromethane sulfonate and hexafluoroacetylacetonate promoters for the activation of palladium catalysts in a polar aprotic solvent.

EXAMPLES 57–62

Hydroformylation of M3P with (DPPF)PtC2H4+DPPF+Promoter

The experiment in Example 1 was repeated except that the platinum catalyst precursor was (DPPF)PtC2H4, additional DPPF was added to maintain the 1.26/1 ligand/Pt ratio and the promoter and water were varied. The results are summarized in Table 8.

TABLE 8

| Ex | Promoter (P) | (P)/P+ | H$_2$O/ (P) | Conv | Sel to M5FV | Lin |
|---|---|---|---|---|---|---|
| 57 | La(OSO$_3$CF$_3$)$_3$ | 2 | 0 | 19 | 86 | 93 |
| 58 | Nd(HFAA)3 | 2 | 0 | 31 | 84 | 93 |
| 59 | Sc(OSO$_3$CF$_3$)$_3$ | 1 | 0 | 75 | 47 | 80 |
| 60 | La(OSO$_3$CF$_3$)$_3$ | 1 | 2 | 14 | 85 | 92 |
| 61 | La(OSO$_3$CF$_3$)$_3$ | 1 | 4 | 22 | 86 | 93 |
| 62 | La(OSO$_3$CF$_3$)$_3$ | 1 | 8 | 28 | 86 | 93 |

These examples show that the ligand may be incorporated into the Pt precursor, that the initial oxidation state of the catalyst may be zero and that catalyst activity increases as the ratio of triflate to Pt increases.

I claim:

1. A process for the preparation of linear aldehyde which comprises contacting a linear olefin, hydrogen, water, and carbon monoxide in a solvent containing a dissolved catalyst comprising: (a) a platinum or palladium compound free of anionic halide, (b) a bidentate diaryl phosphine ligand where each of the aryl groups contain up to 15 carbon atoms and where the bridging group contains 3 to 6 carbon atoms or is a ferrocenyl group, and (c) a promoter selected from the group consisting of (i) a metal perfluoroalkane sulfonate where the alkane has 1 to 10 carbon atoms, (ii) a metal perfluoro-betadiketonate of up to 11 carbon atoms, and (iii) a metal trifluoroacetate; where the metal in (i), (ii), and (iii) is selected from the group consisting of aluminum, scandium, nickel, zinc, yttrium, zirconium, tin, lanthanum, and lanthanide elements from praseodymium to lutetium; where the ratio of (c) to (a) is in the range of 0.5/1 to 20/1, and the ratio of (b) to (a) is in the range of 0.8/1 to 1.5/1.

2. The process of claim 1 in which the olefin contains 2 to 10 carbon atoms.

3. The process of claim 1 in which the olefin is 3-pentenenitrile and the linear aldehyde is 5-formylvaleronitrile.

4. The process of claim 1 in which the olefin is a methyl pentenoate and the linear aldehyde is methyl-5-formylvalerate.

5. The process of claim 1 in which the solvent is selected from the group consisting of acetonitrile, dimethyladipate, dimethylacetamide, dimethylformamide, valerolactone, methylisobutylketone, methylene chloride, toluene, mixtures of a nitrile and toluene, and mixtures of a nitrile and water.

6. The process of claim 1 in which the temperature is in the range of 80° to 120° C. and the carbon monoxide pressure is in the range of 500 to 3000 pounds per square inch.

7. A composition comprising solvent containing a dissolved catalyst comprising: (a) a platinum or palladium compound free of anionic halide, (b) a bidentate diaryl phosphine ligand where each of the aryl groups containing up to 15 carbon atoms, where the bridging group contains 3 to 6 carbon atoms or is a ferrocenyl group, and (c) a promoter selected from the group consisting of (i) a metal perfluoroalkane sulfonate where the alkane has 1 to 10 carbon atoms, (ii) a metal perfluoro-betadiketonate of up to 11 carbon atoms, and (iii) a metal trifluoroacetate; where the metal in (i), (ii), and (iii) is selected from the group consisting of aluminum, scandium, nickel, zinc, yttrium, zirconium, tin, lanthanum, and lanthanide elements from praseodymium to lutetium; where the ratio of (c) to (a) is in the range of 0.5/1 to 20/1, and the ratio of (b) to (a) is in the range of 0.8/1 to 1.5/1.

8. The composition of claim 7 in which the solvent is selected from the group consisting of acetonitrile, dimethyladipate, dimethylacetamide, dimethylformamide, valerolactone, methylisobutylketone, methylene chloride, toluene, mixtures of a nitrile and toluene, and mixtures of a nitrile and water.

9. The process of claim 1 in which the ratio of water to metal promoter is within the range of 1:1 to 200:1.

10. The process of claim 1 in which the olefin is selected from the group consisting of methylpentenoate and a pentenenitrile.

11. The process of claim 1 in which the carbon monoxide partial pressure is in the range of 500 to 3000 pounds per square inch.

\* \* \* \* \*